United States Patent [19]
Landegren et al.

[11] Patent Number: 4,988,617
[45] Date of Patent: Jan. 29, 1991

[54] METHOD OF DETECTING A NUCLEOTIDE CHANGE IN NUCLEIC ACIDS

[75] Inventors: Ulf Landegren; Leroy Hood, both of Pasadena, Calif.

[73] Assignee: California Institute of Technology, Pasadena, Calif.

[21] Appl. No.: 173,280

[22] Filed: Mar. 25, 1988

[51] Int. Cl.$^5$ .................. C12Q 1/68; C12Q 1/00; C07H 15/12; C12N 15/00

[52] U.S. Cl. .................. 435/6; 435/975; 436/501; 436/819; 536/27; 536/78; 536/81; 935/77; 935/78

[58] Field of Search .......... 435/6, 7; 436/501, 819; 536/27, 78, 81; 935/77, 78

[56] References Cited
FOREIGN PATENT DOCUMENTS
0185494 12/1986 European Pat. Off.
0246864 11/1987 European Pat. Off.

Primary Examiner—Amelia Burgess Yarbrough
Assistant Examiner—Mindy B. Fleisher
Attorney, Agent, or Firm—Flehr, Hohbach, Test, Albritton & Herbert

[57] ABSTRACT

Assay for determing the nucleic acid sequence in a region of a nucleic acid test substance having a known normal sequence and a known possible mutation at at least one target nucleotide position. Oligonucleotide probes are selected to anneal to immediately adjacent segments of a substantially complementary test DNA or RNA molecule. The target probe has an end region wherein one of the end region nucleotides is complementary to the normal or abnormal nucleotide at the corresponding target nucleotide position. A linking agent is added under conditions such that when the target nucleotide is correctly base paired, the probes are covalently joined and if not correctly base paired, the probes are incapable of being covalently joined under such conditions. The presence or absence of linking is detected as an indication of the sequence of the target nucleotide.

28 Claims, 9 Drawing Sheets

MATCHED TEST SUBSTANCE | MATCHED TEST SUBSTANCE (A)

TARGET PROBE
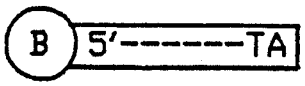
ADJACENT PROBE
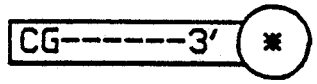

ADJACENT PROBE
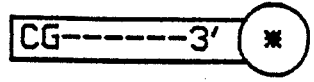
TARGET PROBE
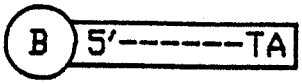

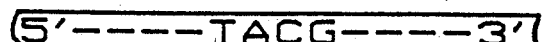
TEST SUBSTANCE

TEST SUBSTANCE (B) DENATURE ANNEAL AND LIGATE

LINKED PROBE PRODUCT
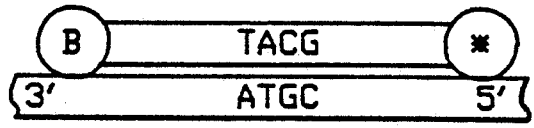

DEATURE MIX WITH BIOTIN BINDING SUPPORT (C) BOUND LINKED PROBE PRODUCT
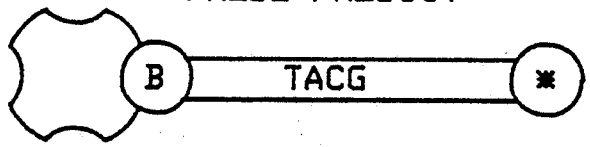

BOUND TARGET PROBE
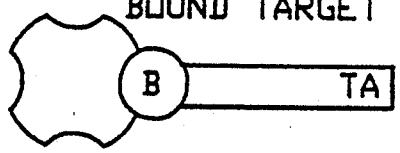

ADJACENT PROBE
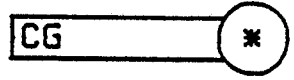

ISOLATE BY FILTRATION (D) BOUND LINKED PROBE PRODUCT
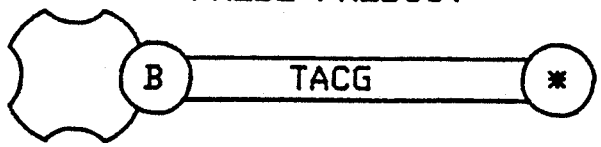

BOUND TARGET PROBE
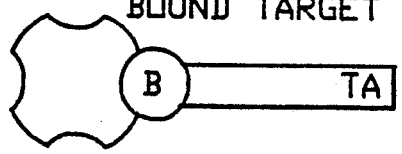

TARGET PROBE B-131 | ADJACENT PROBE P-133

β^A CODING STRAND  5'-ATG GTC CAC CTG ACT CCT GAG GAG PAG TCT GCC GTT ACT-3'
                  3'-TAC CAG GTG GAC TGA GGF CTC CTC TTC AGA CGG CAA TGA-5'

AMINO ACID ENCODED — val-his-leu-thr-pro-glu-glu-lys-ser-ala-val-thr—
AMINO ACID POSITION —  1 - 2 - 3 - 4 - 5 - 6 - 7 - 8 - 9 - 10 - 11 - 12 —

FIG.-2-B

TARGET PROBE B-132 | ADJACENT PROBE P-133

β^S CODING STRAND  5'-ATG CTG CAC CTG ACT CCT GTG GAG PAG TCT GCC GTT ACT-3'
                  3'- TAC GAC GTG GAC TGA GGA CAC CTC TTC AGA CGG CAA TGA-5'

AMINO ACID ENCODED — val-his-leu-thr-pro-val-glu-lys-ser-ala-val-thr—
AMINO ACID POSITION —  1 - 2 - 3 - 4 - 5 - 6 - 7 - 8 - 9 - 10 - 11 - 12 —

LENGTH IN NUCEOTIDES

METHOD OF DETECTING A NUCLEOTIDE CHANGE IN NUCLEIC ACIDS

TECHNICAL FIELD

The present invention relates to the analysis of DNA or RNA, particularly for disease diagnosis.

BACKGROUND OF THE INVENTION

Nucleic acid analysis, particularly for DNA, is becoming important in the diagnosis of infectious as well as genetic disease (Caskey, C. T. (1987), Science, 236, 1223). The inheritance of a substantial number of disease traits can be predicted by analysis of genetically linked markers such as restriction fragment length polymorphisms (RFLP). Moreover, for an increasing number of genetic diseases, the genes involved have been identified and mutant alleles characterized. The more common genetic diseases fall in either of two broad categories: those that can be attributed to any of several independent mutational events, typically seen in X-linked recessive diseases and those that are caused by homozygosity for one of a few alleles, which may be maintained at an appreciable level in the population because of an advantage to the heterozygous carriers (Rotter, J. I., et al. (1987), Nature, 329 287). The characterization of such common disease causing alleles makes large scale screening for carrier status a possibility, limited by the cumbersome nature of the available detection methods.

Recent estimates indicate that about 85% of mutations occurring in the human genome are point mutations, that is they involve a very short sequence of nucleotides. Such mutations typically comprise substitutions of at least one nucleotide for another. This is in contrast to grosser changes such as deletions, insertions, inversions or duplications of longer DNA sequences. Current detection procedures capable of detecting single base substitutions include procedures based on differential denaturation of mismatched probes, as in allele specific oligonucleotide hybridization (Wallace, R. B., et al. (1979), Nucl. Acids Res., 6, 3553) or denaturing gradient gel electrophoresis (Myers, R. M., et al. (1985), Nature. 313, 495). Alternately, the sequence of interest can be investigated for abberations using restriction enzymes as in RFLP analysis (Geever, R. F. (1987), Proc. Natl. Acad. Sci. USA. 78, 508) or using RNAse A to cleave a mismatched nucleotide of an RNA probe hybridized to a target molecule (Myers, R. M., et al. (1985), Science, 230, 1242; Winter, E., et al. (1985), Proc. Natl. Acad. Sci. USA, 82, 7575). While the two techniques using denaturing gradient gels or RNAse A have the advantage of surveying long stretches of DNA for mismatched nucleotides, they are estimated to detect only about half of all mutations involving single nucleotides. Similarly, it is suggested that only approximately one third of the nucleotides in the human genome can be analyzed as part of restriction enzyme recognition sequences. The only existing technique capable of identifying any single nucleotide differences, short of sequencing, is allele specific oligonucleotide hybridization. This technique involves immobilizing separated (Wallace, supra) or enzymatically amplified fragments of test DNA (Saiki, R. K., et al. (1986), Nature, 329, 166), hybridizing with oligonucleotide probes, and washing under carefully controlled conditions to discriminate single nucleotide mismatches.

Whiteley, N. M. et al., EPO Publication No. 0 185 494, discloses an assay in which target sequences in nucleic acids are identified using two oligonucleotide probes of different length (e.g. a 15-mer and a 65-mer), selected to hybridize to contiguous regions of a target nucleic acid which has been previously immobilized. One of the probes is labeled. The short probe includes a potential mutation. Hybridization and/or washing is stated to be performed under conditions of stringency so specific that one probe complementary to a particular sequence will not hybridize (or remain hybridized during high stringency washes) if it is mismatched in one position. If hybridization of both probes occurs under high stringency conditions, the two probes are joined by ligation. Hybridization and ligation is determined by detecting whether label is incorporated in a ligated product. The presence of the label is stated to be an indication of the matching, at the selected stringency, of the short probe with the target nucleic acid sequence. However, this technique is subject to imprecision in that the stringency conditions of hybridizing are difficult to adjust so accurately that they can distinguish hybridization differences based upon a single base pair mismatch.

The references discussed above are provided solely for their disclosure prior to the filing of the instant case, and nothing herein is to be construed as an admission that such references are prior art or that the inventors are not entitled to antedate such disclosure by virtue of prior invention or priority based on earlier filed applications.

SUMMARY OF THE INVENTION

In accordance with the present invention, an assay is provided for determining the nucleic acid sequences in a region of a nucleic acid test substance, typically DNA or RNA, of a type having a known normal sequence and a known possible mutation at at least one target nucleotide position. At least two oligonucleotide probes are selected to anneal (hybridize) to immediately adjacent segments of a substantially complementary test DNA or RNA molecule. One of the probes (the target probe) has an end region consisting of the end nucleotide at the probe junction and one or more nucleotides removed therefrom (the positions collectively called "the target probe end region"), wherein one of the end region nucleotides is complementary to and therefore capable of base pairing with either the normal or abnormal nucleotide at the corresponding target nucleotide position. A linking agent, preferably a ligase, is added under conditions such that when the target nucleotide is correctly base paired, the probes are covalently joined and if not correctly based paired the probes are incapable of being covalently joined under such conditions. The annealed probes are separated from the test substance, as by denaturing. Then, the presence or absence of linking is detected as an indication of the sequence at the target nucleotide. This procedure is capable of identifying known mutations in samples of genomic DNA.

The present invention specifically provides a technique for detecting one or more point mutations in biologically derived DNA or RNA test molecules, such as genomic DNA or mRNA. The use of a ligase to determine base pairing in the end region of a probe sets this technique apart from other methods dependent on differential denaturation of probes which are matched or mismatched to a test nucleotide sequence.

The technique includes the steps of (a) annealing an oligonucleotide target probe of predetermined sequence to a first sequence of a test substance so that said target nucleotide position is aligned with a nucleotide in an end region of the target probe, (b) annealing an adjacent oligonucleotide probe of predetermined sequence to a second sequence of said test substance contiguous to said first test substance sequence, so that the end region of said target probe is directly adjacent to said adjacent probe, (c) contacting said annealed target and adjacent probes with a linking agent under conditions such that the directly adjacent ends of said probes will link to form a linked probe product unless there is nucleotide base pair mismatch between the target probe and test substance at the target nucleotide position, (d) separating said test substance from said annealed probes, and (e) detecting whether or not linking occurs as an indication of nucleotide base pair matching or mismatching at said target nucleotide position.

In a preferred embodiment, at least one of the target or adjacent probes includes a label which is detected. One way to accomplish this is to label only one of the probes and to immobilize the non-labeled one before or after linking. The immobilized probe fraction, containing the linked probe product, is then melted from the test substance and separated from the remainder of the medium. If the label is present on the immobilized probe fraction, this indicates that linkage has occurred.

In another embodiment, the reaction mixture of steps (a) through (d) is placed into a migration substance, such as a gel, in which the probes are caused to migrate, e.g. by electrophoresis. If the two probes are linked to form a linked probe product, it travels at a different rate than the unlinked probes, and so its presence may be detected by observing the position of the label in the migrating medium.

In another embodiment, a diagnostic kit for the detection of abnormalities in the DNA or RNA test substance is provided. The kit includes a container of a first target probe capable of annealing to a first portion of the test substance. The target probe has a nucleotide end region complementary to the normal or mutated nucleotide at the mutation position, i.e. the target nucleotide position. The kit also includes a probe capable of serving as an adjacent oligonucleotide probe for annealing to a second portion of the test substance contiguous to the first portion. Preferably, one of the probes is labeled and the other one is immobilized or includes a binding moiety capable of being immobilized. A covalent linking agent, such as a ligase, may also be included.

BRIEF DESCRIPTION OF THE DRAWINGS

FIG. 1 is one diagnostic approach in accordance with the present invention.

FIGS. 2A and 2B illustrate two typical sequences of target oligonucleotide probes and adjacent probes for determining alleles encoding normal and sickle-cell globin. One oligonucleotide probe is specific for the globin $\beta^A$ gene and the other for the globin $\beta^S$ gene.

DETAILED DESCRIPTION OF PREFERRED EMBODIMENT

Figure 3:
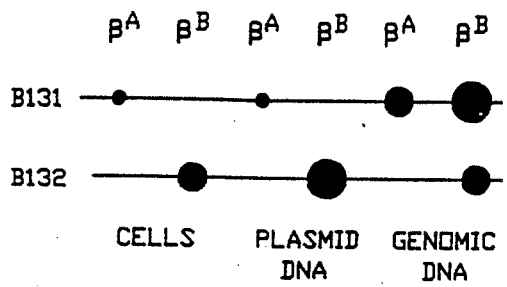
FIG. 3 illustrates the detection of the $\beta^A$ and $\beta^S$ globin alleles contained in plasmid DNA, genomic DNA and nucleated cells.

The assay of the present invention is particularly useful for analyzing nucleic acids (a DNA or RNA test substance) for the diagnosis of infectious and genetic disease. A major advantage of the technique is that it uses two complementary phenomena to provide an exquisitely sensitive overall composite assay for determining the presence or absence of a point mutation in the test substance. One technique is the use of oligonucleotide probes which are complementary to two contiguous predetermined sequences of the test substance. These are the target and adjacent probes in FIG. 1. If these probes anneal in a juxtaposed position, there is a reasonable certainty that the sequences being investigated is the relevant one. In addition, the nucleotide sequences of the oligonucleotide probes are selected so that the target nucleotide is positioned to determine if base pairing with the end region of the target probe occurs. In other words, the target probe end region is aligned with the known position of the point mutation. The annealed probes are then exposed to a linking agent which will link the adjacent ends of the probes only if the nucleotides base pair at the target nucleotide position. Then, the presence or absence of ligation is determined by one of a number of techniques to be described below. In FIG. 1, the technique depicted involves denaturation to produce a single stranded linked probe product or only unligated target and adjacent probes if no ligation occurs. The 5' end of the linked probe product has biotin attached thereto ("B") and a label such as $^{32}P$ attached to the 3' end ("*"). The denatured reaction mixture is then contacted with a biotin binding support such as stretavidin bound to a solid support. This permits isolation of the target probe if no ligation occurs or the isolating of the labelled linked probe product if ligation has occurred. This technique and others disclosed herein provides for the positive identification of each possible allele thereby permitting the identification of heterozygous and homozygous states.

A typical DNA test substance is a portion of a gene of known sequence associated with a known possible genetic disease caused by a single nucleotide mutation. One such disease is sickle-cell anemia. In this instance, the normal and abnormal DNA test substance used in the assay are allelic. The assay may be performed with test DNA derived from purified genomic DNA or may be performed in situ with the test DNA present in cells.

The normal nucleotide and amino acid sequence of the relevant portion of the $\beta$-globin gene is shown in FIG. 2A. The same relevant portion of the nucleotide in the amino acid sequence of the sickle cell gene is shown in FIG. 2B. As can be seen, a point mutation in the codon for amino acid 6 (GAG) results in the substitution of the normal amino acid glutamine in position 6 with the amino acid valine. Thus, in sickle cell disease, a single point mutation results in the substitution of one amino acid for another.

In accordance with the invention, three probes are shown in FIGS. 2A and 2B which may be used to detect the presence of the normal β-globin gene or sickle β-globin gene. These probes are designated P-133, B-131 and B-132. (The "P" designation indicates that a probe is labeled with $^{32}$P at its 5' terminus whereas the "B" designation indicates the probe has biotin attached to it at its 5' terminus.) As indicated, the B-131 and P-133 probes are complementary to the relevant nucleotide sequence in the normal β-globin gene whereas the two probes B-132 and P-133 are complementary to the relevant portion of the $β^S$ globin gene. The probes B-131 and B-132 are the target probes which are identical except for their end region which is contiguous with the adjacent probe P-133. As indicated, the 3' end of the B-131 probe ends with the nucleotide A which is complementary to the nucleotide T in the non-coding strand of normal β-globin. The target probe B-132, on the other hand, has an end region containing the terminal nucleotide T which is complementary to the A which is present in the non-coding strand in the relevant portion of the $β^S$ allele. As will be shown, these probes (or probes representing the complementary sequence) can be readily used to distinguish DNA encoding normal β-globin from DNA encoding sickle β-globin.

In addition to directly detecting point mutations within a structural gene, the assay of the invention may also be used to indirectly detect the presence of normal or defective structural genes. Thus, for example, various DNA sequence polymorphisms genetically linked to the structural gene for known genetic defects are known to be highly correlated with that particular defect. Thus, in the case of sickle cell disease, a linked HpaI restriction endonuclease polymorphism has been found to be highly correlated with the $β^S$ defect. (Kan, Y. W., et al. (1978), *Proc. Natl. Acad. Sci.*, 75, 5631). In this case, appropriate target and adjacent probes can be designed and synthesized to detect the presence of the HpaI restriction site thereby permitting detection of a marker linked to the $β^S$ allele. The indirect determination of a gene defect is most practical when a particular polymorphism is highly correlated with a defective phenotype. Thus, linked markers are useful, for example, when the defect is not known (e.g. Huntingtons disease) or when there are many different defective alleles (e.g. Lesch Nyhans disease). In either case it may be possible to follow the inheritance of these disorders and the prenatal diagnosis thereof, if a known polymorphism is associated with the particular defect which may be detected by the assay of the invention.

The system can also be used to detect RNA sequences, e.g. those present in populations of mRNA molecules expressed in different tissues or rRNA molecules characteristic of specific infectious organisms, by use of complementary DNA or RNA probes. Preferably, inhibitors of the enzyme ribonuclease should be added to prevent degradation of the RNA. Assays for RNA are of value for example, in the quantitative analysis of gene expression in various tissues and in the analysis of infectuous organisms expressing multiple copies of known RN molecules.

DNA probes are preferred for a DNA or RNA test substance because of their ease of synthesis and stability. DNA probes are suitably synthesized in an automated fashion using an automated DNA synthesis instrument such as Applied Biosystems, Inc. model 380A DNA Synthesizer or may be formed by other methods known to those skilled in the art.

Conditions for annealing DNA probes to DNA test substances and to RNA test substances are well known, e.g. as described in *Nucleic Acid Hybridization, A Practical Approach*, Eds. B. D. Homes and S. J. Higgins, IRL Press, Washington, D.C. (1985) and by Wetmur, J. G. and Davidson, N. (1968), Mol.Biol., 31 349. In general, whether such annealing or hybridization takes place is influenced by the length of the probes and the test substances, the pH, the temperature, the concentration of mono-and divalent cations, the proportion of G and C nucleotides in the hybridizing region, the viscosity of the medium and the possible presence of denaturants. Such variables also influence the time required for hybridization. The preferred conditions will therefore depend upon the particular application. Such conditions, however, can be routinely determined without undue experimentation.

A critical feature of the present invention is the careful selection of the adjacent ends of the two oligonucleotide probes. The target probe when annealed to the test DNA or RNA sequence is selected so that the probe end region is positioned over the target nucleotide. In this regard, the end region of the target probe (which contains a nucleotide complementary to the target nucleotide in the normal or abnormal test substance) consists of the end nucleotide (i.e., the 5' or 3' nucleotide immediately adjacent to the adjacent probe) and one, two, or more nucleotides removed from the target probe terminal nucleotide. This end region may extend from the end nucleotide through about the third nucleotide from the juncture point with the adjacent probe. As indicated in the examples, the end nucleotide in the target probe and the nucleotide immediately adjacent thereto in the target probe are nucleotide positions which if not properly base paired with the first sequence of a test substance results in substantially no ligation between the test and adjacent probes, whereas if proper base pairing is present, ligation occurs. However, the base pair matching/mismatching between the target nucleotide and complementary/non-complementary nucleotide in the test probe that will effect ligation is believed to extend beyond the second nucleotide in the end region such that ligation occurs, or fails to occur, because of base pair matching or mismatching in the third nucleotide in the target probe. Thus, the target probe end region can be defined functionally as any of those nucleotides extending from the 5' or 3' end of the target probe immediately contiguous with the adjacent probe which when base pair mismatched with the corresponding target nucleotide in the test substance results in substantially no ligation between the target and adjacent probes The system detects whether or not the two probes are linked in the presence of the linking agent. Annealing and ligation may be performed simultaneously under appropriate conditions. Alternatively, it may be desired to perform the steps sequentially so that pre-selected conditions adapted for annealing may be utilized and other conditions adapted for ligation may be used for that step.

1. Homogeneous Annealing and Liqation

In one embodiment of the invention, both probes are initially in solution phase and the reaction is carried out in solution. For simplicity the system will be described with respect to DNA probes and DNA test substances. A DNA test substance containing a selected region which may contain a point mutation is denatured by conventional means. One of the probes is labeled. The other one is attached to a first binding moiety which is capable of being subsequently immobilized by attachment to a second immobilized binding moiety.

The two probes are selected to be substantially complementary to the selected region of the DNA test substance and directly adjacent to each other in a head to tail relationship. It is important that the region suspected of containing the mutant nucleotide is selected to be in the target probe end region which may be in either the labeled or unlabeled probe. It is preferable to select the terminal or end nucleotide because ligation would be most sensitive to mismatching at that position. However, one or more of the immediately adjacent nucleotides may be selected to align with the target nucleotide. This may be preferable when, for example, the target nucleotide corresponds to one of two adjacent nucleotides in a codon which may be separately mutated to produce a known mutant amino acid substitution. Thus, it is possible to simultaneously assay several target nucleotide positions for complementarity to two target probes (containing separably detectable labels) each of which is complementary to one of two possible nucleotide target positions (or one or more different nucleotides at a single nucleotide target position).

The ultimate size and sequence of the oligonucleotide probes to be used will be determined by the functions which they perform. For example, the probes (except for the target probe end region as discussed elsewhere herein and the corresponding "end region" of the adjacent probe contiguous with the target probe) are selected to be "substantially" complementary to the selected regions of hybridization of the test DNA or RNA. For this purpose, although it is preferable for the probes to match the exact sequence of the test substance template, this is not necessary if, under the conditions of annealing, the probes will hybridize with the test regions. Thus, the stringency conditions of annealing should be selected so that this occurs when the probes are sufficiently complementary to permit annealing of the probe to a complementary selected region of the test substance or to one containing a limited number of internal variations. In the latter case, it is well known to those skilled in the art that a certain number of mismatches may be tolerated within an oligonucleotide probe, vis-a-vis the ability of that probe to hybridize to a particular DNA sequence under given conditions.

The number of mismatches that can be tolerated is dependent upon the number of nucleotides in a particular probe. Thus, as a general rule of thumb, each nucleotide added to a given probe will increase the melting temperature of its corresponding DNA duplex by about 3° C. However, an internal mismatch between the oligonucleotide probe and the substantially complementary DNA strand reduces the melting temperature by approximately 5° C. In general, the longer the probe, the greater the number of internal mismatches that may be tolerated under the given hybridization conditions. Thus, the annealing conditions and/or probe lengths may be selected to permit annealing to nucleic acids having non-conserved regions, e.g., DNA or RNA from organisms that are known to mutate at a high rate (e.g. HIV) if determining the presence of such organisms. On the other hand, stringency should be sufficient to prevent the two probes from fortuitously hybridizing in an incorrect region of the test substance.

Since there is flexibility in the stringency with which annealing may occur, it is possible to simultaneously investigate several different loci in a given test sample for different point mutations. In so doing, test and adjacent probes unique for other point mutations may be employed simultaneously with other sets of target and adjacent probes (provided there are means to detect the ligation of each set of target and adjacent probes). Since each set of probes may have a variable G/C content the probes annealed to a test substance may have variable stability and therefore melt (denature) at different temperatures. However, since there is no need to finely tune the stringency conditions in practicing the present invention, a simultaneous assay at multiple loci is possible.

As indicated, the length of the oligonucleotide probes affects the conditions of annealing. If the probes are too short, stable hybridization may not occur when the probe is internally mismatched in a region away from the target nucleotide. On the other hand, if the probes are too long, it may be possible to anneal in a region other than that of the predetermined target template.

Another factor relating to probe length is the complexity of the DNA test sample. In the human genome, it is estimated that there is a non-repeating length of about $3 \times 10^9$ nucleotides. Thus, to prevent incorrect annealing and ligation of the probes, the combined length of the target and adjacent probes should be of the order of 19 nucleotides or longer. This represents the approximate lower limit in the overall length of the two probes. Thus, a 9-mer and 10-mer could be used as target and adjacent probes.

If the test DNA used in the assay is amplified, such as by the method "polymerase chain reaction" described by Saiki, et al. (1985), *Science*, 230, 1350–1354, shorter probes can be used. This is because there is less likelihood for nonspecific annealing due to the fact that the regions selectively amplified by such techniques comprise a very small portion of, for example, the human genome thereby reducing the complexity of the sample being assayed.

Excellent results are obtained whether assaying genomic or amplified DNA samples with probes that are in the range of 16–20 nucleotides in length. Longer probes such as 30-mers, or longer, may also be used.

For detection, any known label for proteins, peptides or nucleic acids may be used in accordance with the present invention. Such labels include radioactive tags, enzymes, fluorescent tags, and colorimetric tags.

Specifically, one preferred form of labelling is to add phosphorous 32 ($^{32}P$) to the 5' hydroxyl group of the oligonucleotide probe using the enzyme polynucleotide kinase. Other labels can be used such as iodine 125 ($^{125}I$) although labeling with this radioisotope would be less convenient. The oligonucleotides can also be labeled with organic fluorophors such as carboxy-fluorescein or carboxy-2,7-dimethoxy-4,6-dichlorofluorescein, e.g. by coupling to a 5' aminothymidine in the probe. Also, chelated rare earth metal ions such as $Eu^{3+}$ and $Te^{3+}$ may give a high signal to noise ratio permitting sensitive detection utilizing time resolved fluorescence techniques (Soini, et al. (1983), Clin. *Chem.*, 27 65). In addition, enzymes may be attached to one of the probes and used as a detection label analogous to an ELISA assay (Jablonski, et al. (1986), *Nucl. Acids Res.*, 14, 6115).

In general, it is desirable to use fluorescent rather than radioactive probes. Advantages to this approach include safety aspects, stability of the reagents, and immediate access to the result. In addition, fluorescent detection permits multicolor analysis whereby the presence of alternate alleles or a quantitative comparison of two genes can be analyzed in an internally controlled fashion.

In some instances, it may be desirable to increase the amount of test DNA before the assay of the invention using the recently described polymerase chain reaction (Saiki, et al. (1985), *Science.* 230, 1350-1354). Such instances occur, for example, when genes are present at less than one copy per genome equivalent. Examples include rearranged lymphocyte receptor genes in populations of lymphoid cells or parasitic genomes contaminating the host cells at low frequency. In addition, amplification is of value when a limited amount of material is available for analysis. In this amplification procedure a small segment of DNA can be exponentially amplified by repeated cycles of copying of a template DNA to produce new strands from two primers, one with a sequence upstream from, and the other in the opposite orientation downstream from, the DNA segment of interest.

Amplification is performed by cyclically varying the temperature, each cycle including a denaturing step, a step for the annealing of primer oligonucleotides and a step where a DNA polymerase extends a new complementary strand from the primers by incorporating nucleotides.

After amplification, the target and adjacent probes for detecting a normal or abnormal sequence in the amplified DNA segment of interest are added and annealed under the appropriate conditions. Then, during or after annealing, a linking agent is added which is capable of forming a covalent bond between the contiguous probes. A linked probe product is formed if the correct base pairing is present at the juncture of the two probes.

The preferred linking agent is a ligase, preferably T4 DNA ligase, using well known procedures (Maniatis, T. in *Molecular Cloning,* Cold Spring Harbor Laboratory (1982)). Other DNA ligases may also be used. T4 DNA ligase may also be used when the test substance is RNA (*The Enzymes,* Vol. 15 (1982) by Engler M. J. and Richardson C. C., p. 16-17. *Methods in Enzymology,* Vol. 68 (1979) Higgins N. P. and Cozzarelli N. R. p. 54-56). With regard to ligation, other ligases, such as those derived from thermophilic organisms may be used thus permitting ligation at higher temperatures allowing the use of longer probes (with increased specificity) which could be annealed and ligated simultaneously under the higher temperatures normally associated with annealing such probes. The ligation, however, need not be by an enzyme and, accordingly, the linking agent may be a chemical agent which will cause the probes to link unless there is a nucleotide base pair mismatching at the target nucleotide position. The invention will be described using T4 DNA ligase as the linking agent. This enzyme requires the presence of a phosphate group on the 5' end that is to be joined to a 3' OH group on a neighboring oligonucleotide.

Ligation conditions are adjusted so that ligation will occur if there is a base pair match at the target nucleotide position and will not occur if there is a mismatch at that position. Assuming simultaneous annealing and ligation, the ligation may be performed at a temperature below the melting temperature of the annealed oligonucleotide probes. A suitable temperature for this purpose is about 5° C. to 30° C. below the melting temperature of the hybridized sequences. For ligation after hybridization, a suitable temperature is about 37° C. for T4 DNA ligase. In the examples, simultaneous annealing and ligation takes place at about 37° C. Factors that determine whether or not mismatching at the target nucleotide position can be discriminated, as detected by ligation, include salt concentration and the amount of enzyme (ligase) used. Suitable salt concentrations range from 0 to 200mM. Typically, the oligonucleotide probes are present in large excess of the test substance, e.g. $10^3$ times or more. Suitable ligase concentrations range from $10^{-4}$ to about 1 Weiss unit for such probe concentrations. The preferred salt and ligase concentrations are readily determined empirically for a particular application. Thus, as described in Example 5, 150-200 mM NaCl and $0.15-50.0 \times 10^{-3}$ Weiss units of ligase are preferred when T4 DNA ligase is used.

After hybridization and treatment with ligase, ligation of the target and adjacent probes (to produce the "linked probe product") may be detected by a number of techniques. In each of these techniques, it is preferable that the linked probe product (if formed) be separated from the test substance to ensure that ligation rather than only hybridization is being detected. Thus, DNA/DNA or DNA/RNA duplexes containing linked probe product may be denatured by techniques known to those skilled in the art.

The detection of ligation is preferably performed by detecting the label contained by either the target probe or adjacent probe. Thus, for example, ligation can be determined by electrophoretic techniques such as polyacrylamide gel electrophoresis (PAGE) under denaturing conditions. In this technique, unligated labeled probe of known size is separated from labeled linked probe product which is of a known larger size. Thus, ligation may be detected during or after electrophoresis. In the former case, a label detector may be mounted to detect label as it passes a particular point in the electrophoretic medium during electrophoresis. In such a system, unligated label would be detected followed by the linked probe product (if formed) at a predictable time depending upon the location of the label detector and the electrophoretic conditions. Devices capable of detecting fluorescent labels in this manner are known in the art (Smith, L. M. et al. (1986) *Nature* 321:672; Prober, J. M., et al. (1987), *Science,* 238, 336). Alternatively, the electrophoresis may be completed and the label detected by standard techniques such as by autoradiography of radioisotope labelled probes Another technique for detecting ligation employs the immobilization of the linked probe product. In this technique, the adjacent probe contains a first binding moiety which is reactive to a second binding moiety. The second binding moiety is immobilized on a solid support. The adjacent probe containing the first binding moiety together with the target probe containing the label is hybridized with test substance and treated with a ligase. Then, the linked probe product (if formed) containing the first binding moiety is bound to its corresponding immobilized second moiety. One such first binding moiety is biotin which may be covalently attached to the probe by known techniques. The binding moiety is subsequently bound to an immobilized complementary second moiety such as streptavidin immobilized on a solid support such as agarose (Updyke, T., et al. (1984), *J. Immunol. Methods,* 73. 83; Syvanen, et al. (1986), *Nucl. Acids Res.,* 14, 5037). Suitable other pairs of first and second binding moieties are: (a) antigens and antibodies, (b) carbohydrates and lectins, (c) complementary strands of DNA, (d) mutually reactive chemical groups and the like. This permits separation of the linked probe product a discussed below.

The reaction products are preferably denatured prior to binding of the first and second binding moieties to assure that the ligated probes reach the immobilized second binding moiety, e.g. streptavidin coated beads. If this is not a problem, the reaction product may be denatured after immobilizing. In either event, the reaction products are preferably denatured prior to detection so that only ligated products are detected.

After immobilization, the immobilized probe reaction product or fraction is separated from the remainder of the fluid system as by filtration. If the probes anneal and ligate to form the linked probe product, the labeled probe will be covalently bound to the adjacent probe containing the first binding moiety to form a detectable reaction product.

A number of separation techniques for the immobilized probe reaction product may be used. For example, probes bound to beads via a biotin-streptavidin linkage may be separated from free probe by filtration over a membrane. Alternatively, the second binding moiety may be present on a dip stick, introduced into the reaction well at the end of the assay and then washed prior to detection.

Then, the label contained in the separated immobilized reaction product is detected by conventional means. For example, if the label is radioactive, it may be detected by known procedures and instrumentation. The absence of a signal indicates either that (a) the detecting and adjacent probes did not both anneal to the target substance or, if annealed, (b) ligation did not occur.

In essence, annealing places the investigator in the right region of sequence while ligation determines with precision the identification of the specific allele based upon the matching or mismatching of the base pair at the juncture of the probes.

The above system has been described using two probes. However, three or more adjacent probes may be used so long as the probe at one end is or can be immobilized and the one at the other end is labeled. In this manner, mutant nucleotides at multiple junctions may be detected in an analogous manner.

2. Heteroqenous Annealing and Ligation

Instead of performing the assay with two soluble probes and thereafter immobilizing as set forth above, one of the probes or the test DNA or RNA substance may be immobilized on a solid support prior to annealing. When one of these probes is immobilized, the other probe (either target or adjacent probes) is labeled and in solution phase. This permits detection of label immobilized to the solid support based on the discrimination of matching or mismatching at the target nucleotide position by ligation. When the test substance is immobilized, both the labelled and unlabelled probes are soluble in the fluid medium.

Techniques to immobilize DNA, including the probes of the present invention, onto solid supports such as commercially available polymers, nylon or nitrocellulose membranes (see e.g., Maniatis, et al., supra) and dextran supports (Gingeras, T. R. et al. (1987) *Nucl. Acids Res.*, 15, 5372–5390) are well known to those skilled in the art. Other immobilization techniques include attachment of biotinylated probes to immobilized streptavidin, the linking of amino groups on the probe to amino groups on a membrane bound protein support via a bifunctional linking reagent such as disuccinimidyl suberate and the methods described by Bischoff, et al. (1987), *Anal. Biochem.*, 164, 336; Goldkorn, et al. (1986), *Nucl. Acids Res.*, 14, 9171; Jablonski, et al. supra and Ghosh F., et al. (1987) *Anal Biochem*, 164, 336–344. Thus, for example, an adjacent probe may be bound to a solid support and contacted with a DNA test substance under conditions which permit annealing of the adjacent probe to the complementary region of the test DNA sample. Thereafter (or simultaneously therewith) the target probe containing a label is contacted with the test DNA substance to permit annealing of the target probe with the test DNA region immediately adjacent and contiguous to the adjacent probe. If necessary, the temperature is adjusted to maintain enzymatic activity of T4 DNA ligase which is thereafter contacted with the annealed target and adjacent probes to produce ligation if base pair matching in the end region of the target probe is present. Thereafter, the stringency of the fluid medium is raised to remove substantially all the species of the labelled target probe which are not ligated to the adjacent probe. The labelled linked product is then detected by standard techniques by measuring the labelled linked product bound to the solid support.

Alternatively, a biotinylated probe can be immobilized on a streptavidin-coated solid support (e.g., agarose beads) and the assay conducted as described in Example 6.

The biotin-streptavidin binding phenomenon (or for that matter, any other binding phenomenon such as antibody-antigen binding, etc.) may also be utilized in a modified heterogenous assay. Thus, for example, one of the probes may be immobilized on a solid support by standard techniques. A biotinylated soluble probe is then employed in the assay as described. If ligation occurs the biotinylated linked product will be bound to the solid support. Thereafter, any label linked to streptavidin, e.g., radioisotope, enzyme, etc. is contacted with the immobilized biotinylated linked probe product and assayed using standard techniques to ascertain whether the ligation event occurred.

It is also possible to assay for more than one genetic defect at various loci in a genomic DNA sample using immobilized probes. Thus, sets of target and adjacent probes each specific for one of a group of known genetic defects, e.g., point mutations, may be employed. Each of the unlabeled probes from each probe set is immobilized in physically discrete sections on a solid support. In this manner, each discrete location represents a separate test for a particular defect. Thereafter, the DNA test substance is contacted with each of the immobilized probes. A mixture of the labelled soluble probes from each of the above probe sets is then added. Each of these labeled soluble probes is capable of annealing to the test DNA substance in continuity with the immobilized probe. After ligation (if it occurs), non-ligated labelled probe is removed from the solid support and labeled linked probe product immobilized on the solid support is detected. The detection of a labelled linked probe product in a particular discrete location on the support (or the failure to detect such a signal) provides an indication of the base pair matching or mismatching between the target probe and the target nucleotide position for that discrete location. Thus, one or more genetic defects are assayed simultaneously by this method.

Instead of immobilizing one of the probes, the DNA test substance may also be immobilized to a solid support. Thus, for example, test DNA substance is first digested with one or more restriction endonucleases and electrophoretically separated in an agarose gel. Thereafter, the DNA is transferred to a nitrocellulose or nylon membrane by standard techniques. Then, sequences representing different genetic loci, migrating to different positions in the gel, can be simultaneously assayed using the methods disclosed herein. After transfer to the nitrocellulose or nylon membrane, the general binding tendency of the membrane is exhausted using standard techniques prior to exposure to the target and adjacent probes. This prevents nonspecific adsorption of the probes to the membrane. In practicing this aspect of the invention, however, ionic detergents such as SDS should be avoided to prevent inactivation of the ligase used to bring about linking of the target and adjacent probes. The actual annealing and ligation is preformed analogously to that already discussed. Thus, a single set of probes for a particular mutation or a multiplicity of probe sets may be used to detect one or more genetic defects provided that the particular test DNA substance for each mutation being assayed migrates electrophoretically at a different rate than the others being assayed.

The following examples are specific illustrations of the present invention.

EXAMPLE 1

This Example illustrates homogeneous annealing and ligation using soluble probes. Plasmids, human genomic DNA and human nucleated cells were analyzed for the presence of the globin $\beta^A$ and $\beta^S$ gene. Samples of nucleated cells, obtained by Ficoll Hypaque floatation of whole blood from normal and a previously diagnosed homozygous sickle cell patient, were used as a source of DNA for the in situ analysis. One $\times 10^6$ cells from the $\beta^{A/A}$ and $\beta^{S/S}$ donars in 50ul phosphate buffered saline were added to separate wells in round bottom flexible microtiter plates with 10 ug of salmon sperm DNA in 4ul of water. The microtiterplates were centrifuged and supernatants removed. To the pellet was added 1ul of 10% Triton X100 and 1ul of 2ug/ul trypsin. The samples were incubated at 37° C. for 30' and then 1ul of 0.5 N NaOH was added, the samples incubated for 1 minutes at 37° C. and after restoring the pH with 1ul of 0.5 N HCl, one ul of soy bean trypsin inhibitor (Sigma) 10ug/ul was added.

Linearized plasmid molecules containing the $\beta^A$ (pBR328:$\beta^A$−1.9) or $\beta^S$ (pBR328:$\beta^S$1.9) ) allele of the human globin genes (Saiki, et al. (1985), *Biotechnology*, 3, 1008) in amounts equivalent to the $\beta^A$ and $\beta^S$ sequences obtained from the nucleated cells were added to individual wells in a microtiter plate. For detection of genes in genomic DNA, the DNA was extracted, sheared by passage through a syringe needle and 7ug aliquots in 4 ul water added to the wells. The DNA samples were then denatured by the addition of 1ul of 0.5 N NaOH and incubated for 10 min at 37° C. before the pH was restored with 1ul of 0.5 N HCl.

Appropriate oligonucleotide probes were synthesized in an automated fashion on an Applied Biosystems, Inc. Model 380A DNA synthesizer using the $\beta$-cyanoethyl phosphoramidite chemistry (Hunkapillar, M., et al. (1984), *Nature*, 310, 105) and standard cycles as provided by the manufacturer. Subsequent to standard cleavage and deprotection procedures, the crude oligonucleotides were purified either by preparative polyacrylamide gel electrophoresis or by reverse phase high performance liquid chromatography (HPLC) using an octyldecylsilyl (ODS) column (Axxiom, 4.6mm $\times$ 250 mm) and a linear gradient of acetonitrile in 0.1 M triethylammomium acetate, pH 7 (5% to 20% acetonitrile in 30 minutes). Biotinylated e. As the final step in the oligonucleotide syntheses, the cyanoethyl phosphoramidite of N-protected 5'-amino-5'-deoxythymidine was added manually using published procedures (Smith L. et al. (1985) *Nucl. Acids Res.* 13, 2399). After cleavage and deprotection, the crude amino-derivatized oligonucleotide (50 nmols in 200 ul of water plus 50 -100 ul of a1M sodium bicarbonate/carbonate buffer, pH 9.0) was treated with the N-hydroxysuccinimide ester of N-biotinyl-6-aminohexanoic acid (Enzotin, Enzo 3–5 mg/100 ul of N,N-dimethylformamide) for 3 to 8 hours at room temperature. The product was then purified by HPLC as described above. In all cases, biotinylation was nearly quantitative, with the biotinylated oligonucleotide being retained about 3–5 minutes longer on the ODS column than the starting amino oligonucleotide using the above gradient. Biotinylation could also be performed by tailing the 3' end of an oligonucleotide using terminal deoxynucleotidyl transferase and dUTP-biotin (Bethesda Research Laboratories). (Riley, L. K., et al. (1986), *DNA*, 5, 333). Oligonucleotides labelled with $^{32}p$ at the 5'terminus using polynucleotide kinase were purified by chromatography on a Nensorb column (New England Nuclear) using procedures provided by the manufacturer.

Each well received 140 fmol of biotinylated oligonucleotides 131 or 132 corresponding to the sequences shown in FIG. 2 and specific for the globin $\beta^A$ and $\beta^S$ gene, respectively. In addition, 1.4 fmols of the adjacent probe 133 having the sequence shown in FIG. 2 was added. This adjacent polynucleotide kinase to a specific activity of $5 \times 10^8$ Cerenkow cpm/ug. 0.05 Weiss units of T4 DNA ligase (Collaborative Research) was added in 2 ul ligase buffer to a final volume of 10 ul in 50 mM Tris-HCl pH 7.5, 10 mM MgCl2, 150 mM NaCl (including 50 mM added during denaturation), 1 mM spermidine, 1 mM ATP, 5 mM dithiothreitol and 100 ng/ul bovine serum albumine. The reagents were mixed by briefly centrifuging the microtiter plates before incubation at 37° C., 100 % humidity for 5 hours. The reaction was stopped by the addition of 1 ul of 1.1 N NaOH, incubating for 10 minutes at 37° C. followed by 1 ul 1.1 N HCl and 2 ul of 10% sodium dodecyl sulfate (SDS). Three ul of a 15% (v/v) suspension of streptavidin-coated agarose beads (Bethesda Research Laboratories) were added and the plate was incubated on a shaking platform at room temperature for 5 minutes. The contents of the wells were then transferred to a dot blot manifold (Schleicher and Schuell, Keene, New Hampshire) containing a Whatman filter paper #4. In order to reduce nonspecific binding of the labeled streptavidin-agarose beads were added in 0.5% (v/v) dry nonfat milk, 1% SDS and 100 ug/ml salmon sperm DNA. The size of the area on which the beads were deposited was reduced to 2 mm diameter by interposing a 3 mm thick plexiglass disc with conical holes, beads were washed under suction in the manifold with 3 ml 1% SDS and 1ml 0.1 N NaOH per sample, using a 96-tip dispenser (Micropette). The filters were wrapped in plastic wrap and autoradiographed for 4 days at 70° C. with one enhancing screen (DuPont).

The results of this experiment are shown in FIG. 3. As can be seen, the $\beta^A$ globin probe B-131 was successfully ligated to labeled probe P-133 when reacted with DNA samples including the normal $\beta^A$ globin gene sequences obtained from nucleated cells, plasmid and genomic DNA. As further shown in FIG. 3, the $\beta^S$ globin probe B-132 ligated with label probe P-133 when reacted with DNA samples including the $\beta^S$ globin gene sequence obtained from nucleated cells and plasmid and genomic DNA. Thus, the $\beta^S$ globin defect can be readily detected and distinguished from the normal $\beta$-globin gene sequences by the assay of the invention.

EXAMPLE 2

In this Example, the following three probes were used—two different target probes representing normal ($\beta^A$ globin) and abnormal ($\beta^S$ globin) genes, each tagged with two different fluorescent labels and a third adjacent probe having a sequence contiguous with the target probes. Separation and detection of ligation or lack thereof was by the gel migration technique.

Genomic DNA was obtained from three human cell lines: Molt 4 (Saiki, R. K., et al. (1985), *Science*, 230, 1350), which is homozygous for the $\beta^A$ globin gene, SC-1 which is homozygous for the $\beta^S$ gene (Saiki, et al. (1985) *Biotechnology* 3, 1008), and GM1064 in which the $\beta$-globin locus has been deleted (Tuan, D., et al. (1983), *Proc. Natl. Acad. Sci.*, 80, 6937). One μg aliquots of the genomic DNA containing the $\beta$-globin sequence were amplified in 25 cycles. Specifically, 120 nucleotide segments of the normal $\beta$-globin or sickle $\beta$-globin were amplified. The primers used for this amplification were PCO3 and PCO4. (Saiki, et al. (1985) $\beta^S$ *Science* 230:1350 supra.) This resulted in the amplification of a gene sequence containing the potential site of the sickle cell mutation. Aliquots (3 μl), equivalent to approximately 24 ng of genomic DNA, were employed for the ligation reaction without further purification.

In the ligation reaction, two DNA target probes, specific for the $\beta^A$ (probe CF-131) and $\beta^S$ (probe CD-132) genes and differentially labeled with two fluorophores were present at equal concentrations. An unlabeled adjacent probe (probe P-133) was also added. Each of these probes is equivalent to the corresponding numbered probes in FIG. 2 except for the addition of the fluorescent labels to oligonucleotides 131 and 132 and the useof a non radioactive 5'phosphate in oligonucleotide 133.

The CF-131 probe was labeled with carboxyfluorescein. The CD-132 probe was labeled with carboxy-2,7-dimethoxy-4,6-dichlorofluorescein. These probes were labeled essentially as described for the biotinylated probes, using the N-hydroxysuccinimide ester of the appropriate dye (1 mg/100 ul of N,N-dimethylformamide for 50 nmols of amino oligonucleotide). The N-hydroxyduccinimide ester of carboxy-fluorescein was obtained from Molecular Probes (Junction City, Oreg.), and the N-hydroxysuccinimide ester of carboxy-2,7-dimethoxy-4,5-dichlorofluorescein was obtained from Applied Biosystems, Inc. (Foster City, Calif.). After allowing the dye-oligonucleotide reactions to stand overnight in the dark, the mixtures were applied to a 10 ml column of Sephadex G-25 in water to separate the labeled probe (eluted in the void volume of the column) from excess dye (retained on the column). The product was then further purified by HPLC as previously described for purifying biotinylated probes.

Probe CF-131 and CD-132 (14 fmol each) together with adjacent probe P-133 (14 fmol) which hybridizes downstream of either of the other two probes were combined with the above aliquots of genomic DNA obtained from the three different human cell lines. The reaction conditions were essentially the same as in Example 1 except that 0.5 Weiss units of T4 DNA ligase were added to each reaction. At the end of the three-hour incubation period the samples were ethanol precipitated and taken up in 50% formamide.

Figure 4A:
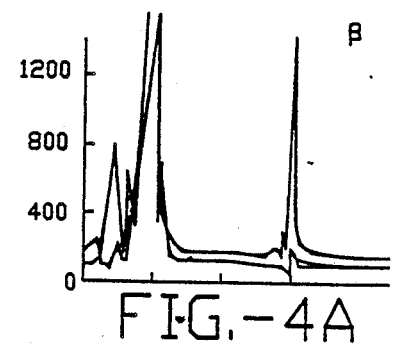
FIG. 4A, 4B and 4C illustrate detection of the $\beta^A$ and $\beta^S$ alleles in nucleated blood cells and the failure to detect such sequences in a gene deletion sample control using differentially labelled target probes.
Figure 4B:
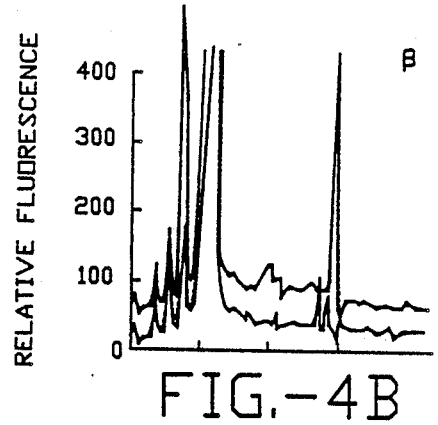
Figure 4C:
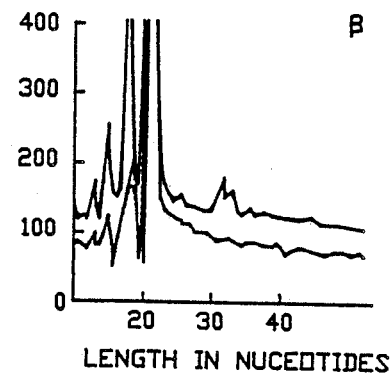

The amount of CF-131 and CD-132 that became ligated to the adjacent probe was determined by separating the reaction products on a polyacrylamide gel and analyzing the band migrating as a 40-mer (the size of CF-131 or CD-132 ligated to probe P-133) for the relative contribution of each of the two different fluorophores. This was done on an Applied Biosystems DNA sequencer, model 370A. The instrument separates and analyses the migration of fluorescence labeled DNA fragments in a polyacrylamide gel (Smith, L. K., et al. (1986), Op Cit. The results are shown in FIG. 4A, 4B and 4C. In each figure, the first group of peaks represents the fluorescent labeled probes which have not been linked, together with other smaller spurious peaks. In FIG. 4A, which is the result obtained using normal $\beta$-globin DNA, a single peak is shown to the right of the first group of peaks. This signal represents a fluorescent linked probe product with the appropriate emmission spectrum for the CF-131 fluorophore as determined by the instrument. It migrates as a 40-mer indicating that it has been ligated to P-133.

Similarly, in FIG. 4B, where the DNA sample was obtained from a cell line homozygous for the $\beta^S$ globin gene, the peak (dashed line) to the right of the first peaks corresponds to a linked probe product having the appropriate emission spectrum for the CD-132 fluorophore. Its position also indicates that it has been ligated to the probe P-133.

FIG. 4C represents the assay of a DNA sample from a cell line that has deleted the $\beta$-globin gene. As can be seen, no signal is observed corresponding to a linked probe product which would be formed if $\beta$-globin DNA sequences were present.

EXAMPLE 3

In the previous examples, probes B-131 and B-132, specific respectively for the $\beta^A$ and $\beta^S$ globin genes, were used. In each case, the terminal nucleotide in each of these target probes determined whether there would be a match or mismatch with the normal $\beta$-globin or abnormal sickle globin gene. This example demonstrates that the end region of the target nucleotide is not limited to the end nucleotide.

Figure 5:
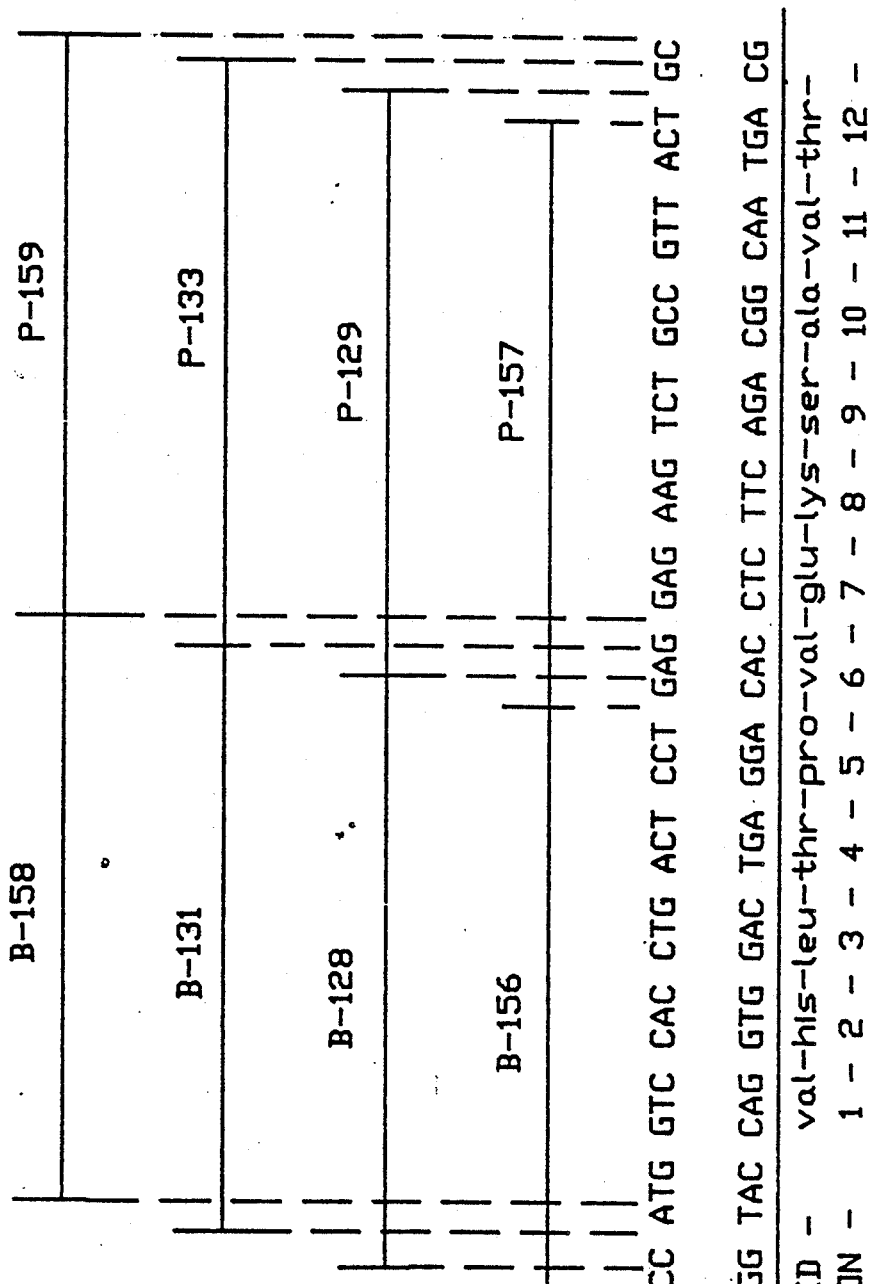
FIG. 5 illustrates the strategy used to determine the effect of nucleotide position on ligation.

The design of this example is shown in FIG. 5. The non-coding complementary DNA sequence for the $\beta^S$ globin gene together with the $\beta^S$ amino acid sequence is shown at the bottom of FIG. 5. Immediately above that nucleotide sequence is the corresponding complementary coding strand sequence for the relevant region of the $\beta^S$ globin gene. Four sets of probes were synthesized. Each contained two 20 mers corresponding to the segments designated in FIG. 5. As can be seen the sets B-131/P-133 and B-128/P-129 correspond to target (B-131 and P-129) and adjacent probes (P-133 and B-128) wherein the end nucleotide of the target probe is positioned to base pair mismatch with the mutated nucleotide in the second position of the 6th codon of the $\beta$-globin gene designated by (*). The probe sets B-158/P-159 and B-156/P-157 contain a mismatch with the mutated nucleotide in the nucleotide immediately adjacent to the terminal nucleotide in the target probe. All of the "P" probes were labeled with $^{32}P$.

In addition, two probe sets specific for detecting the $\beta^S$ globin gene sequence were also used. These probes were designated B-132/P-133 (for sequence, see FIG. 2B) and B-128/P-130. The P-130 sequence corresponds to the sequence of P-129 except that its 3' nucleotide renders it specific for the $\beta^S$ globin allele.

Figure 6:
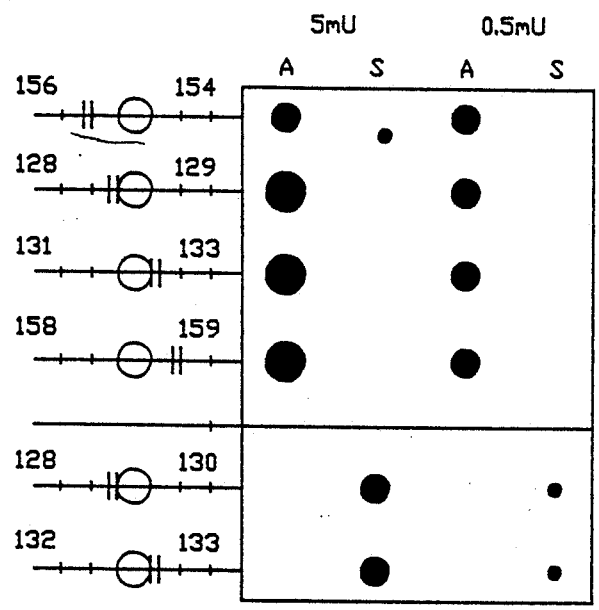
FIG. 6 is an autoradiogram illustrating the results of Example 3.

Each of these probe sets were separately used to assay DNA encoding $\beta^A$ or $\beta^S$ globin in a manner analogous to that described in Example 1 except that varying amounts of ligase were used. The results are shown in FIG. 6. As indicated, the assay discriminates against mismatches in positions −2, −1, +1 and +2 from the ligation junction for normal $\beta$-globin senquences. $\beta^S$-specific reagents, mismatched to the $\beta^A$ globin allele in position −1 and +1 were included as a control.

EXAMPLE 4

This example discloses the detection of a point mutation in a gene sequence other than that contained within the $\beta$-globin gene. In particular, this experiment illustrates the identification of two T cell receptor variable genes which differ by a single nucleotide. The experiment was performed essentially as described in Example 1 except that the assay was done in 1.5 ml Eppendorf tubes, denaturation before and after ligation was by boiling at 100° C., and separation of ligated material from unligated material was achieved by polyacrylamide electrophoresis.

Figure 7:
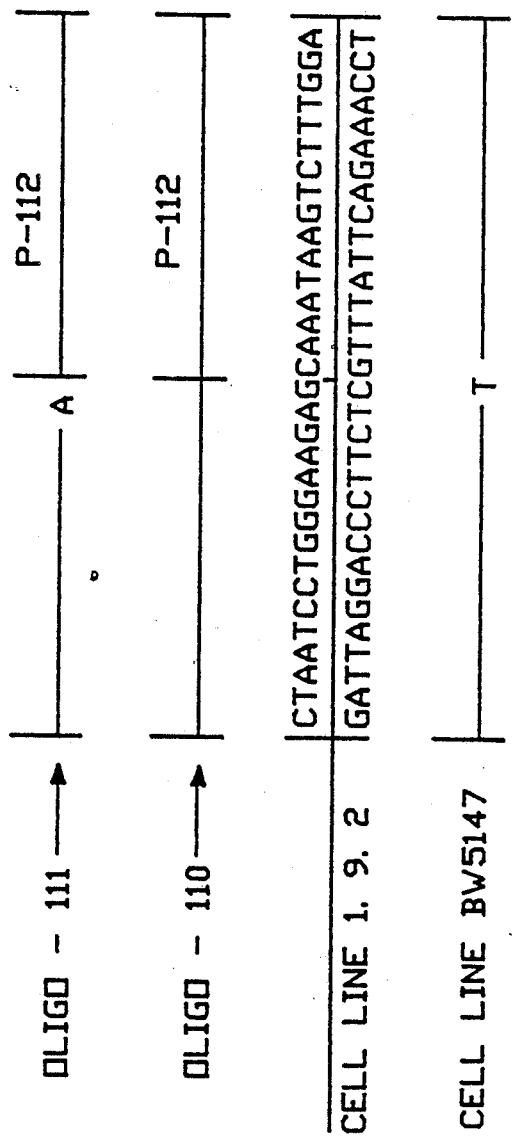
FIGS. 7 and 8 illustrate the strategy employed and results obtained in Example 4.

The particular T cell receptor variable gene investigated was $V_{\beta 1}$ which consists of a dimer of alpha and 62 protein. The sequences of the $V_{\beta 1}$ genes derived from the cell lines BW5147 and 1.9.2 differ in a single nucleotide position (Barth, et al. (1985), *Nature*, 316, 517). The sequences for the relevant region of the DNA from cell line 1.9.2 and cell line BW5147 are shown in FIG. 7. The sequences of the target probe B-110 (compelementary to the sequence in cell line 1.9.2) and B-111 (complementary to the sequence in cell line BW5147) are also shown in FIG. 7 together with the sequence of the adjacent oligonucleotide P112 which was labelled with $^{32}$P at the 5' terminus.

Figure 8:
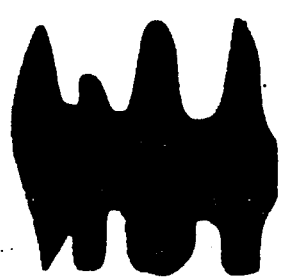

After annealing and ligating each of the sets of probes to each of the test DNA from the two cell lines, the samples were subjected to polyacrylamide gel electrophoresis. The autoradiogram of this experiment is shown in FIG. 8. The low molecular weight signals correspond to unligated $^{32}$P labeled probe P-112. Two signals can be seen in lanes 3 and 4 at the arrow. As indicated, these correspond respectively to probe and B-110 correctly annealing to the complementary test DNA so as to be ligated to probe P-112 to form the 32-mer signals shown. As further indicated in lanes 1 and 4, when there is a mismatch between the target probe and the target nucleotide sequence no ligation occurs as indicated by the failure of a 32-mer to form.

EXAMPLE 5

This example describes the empirical determination of the appropriate conditions for performing the ligation reaction such that any nucleotide mismatch in the target region is discriminated from correct base pairing.

Figure 9:
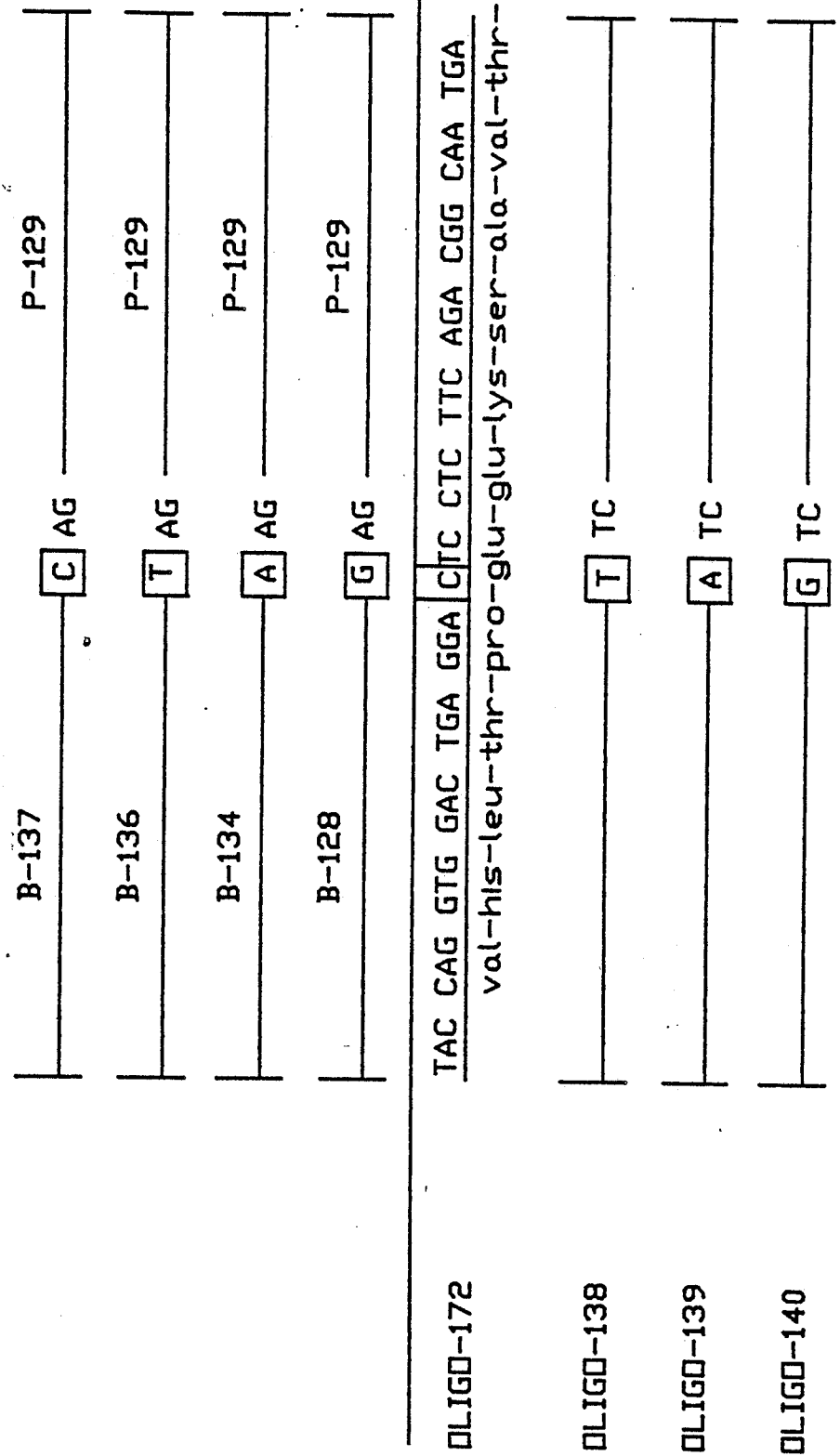
FIGS. 9, 10A and 10B illustrate the strategy employed and results obtained in Example 5.
Figure 10B:
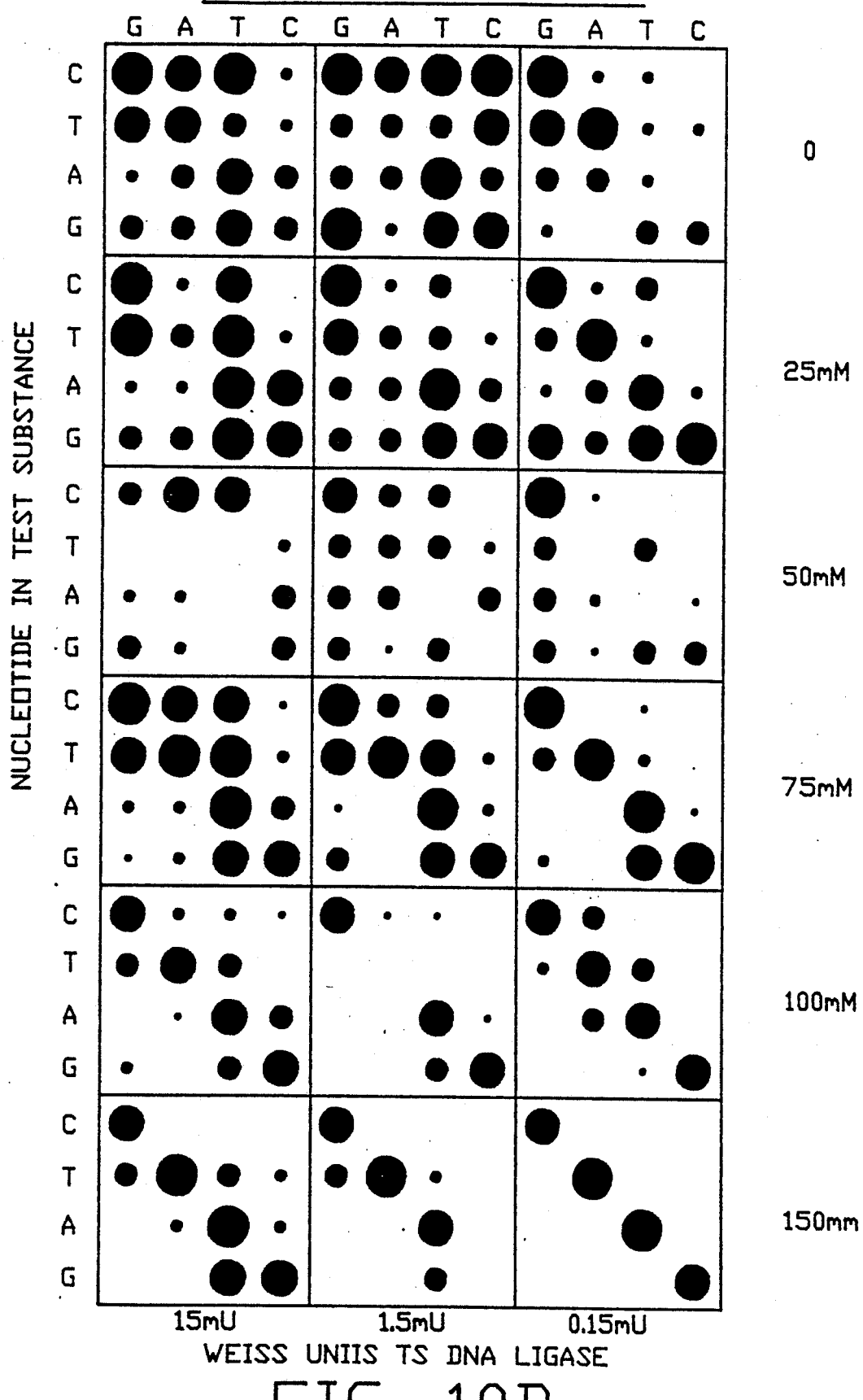
Figure 10A:
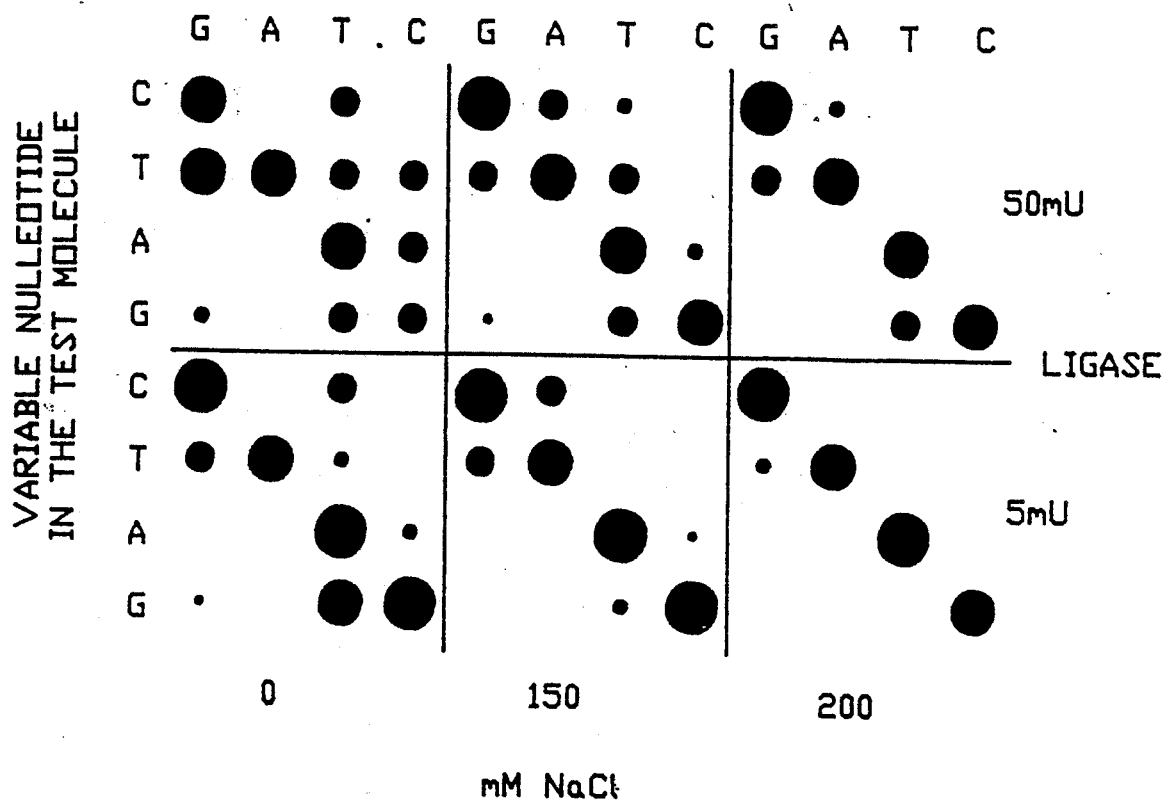

The $\beta$-globin alleles $\beta^A$ and $\beta^C$ differ in the first position of the 6th codon. Test molecules representing these two alleles were synthesized as two 40-mer oligonucleotides, denoted 172 and 138, respectively (see FIG. 9). These oligonucleotides represent the antisense sequence of the alleles and are centered around the variable target nucleotide position in the 6th codon. Two more oligonucleotides of similar sequence, 139 and 140, were synthesized, each including one of the other two possible nucleotides in the variable target nucleotide position. The four molecules are thus of identical sequence except in the target nucleotide position where each oligonucleotide has a different nucleotide. Four 20-mer biotinylated target oligonucleotides, differing only in their 3' nucleotide position, were designed to hybridize to the 3' half of the target molecules in such a manner that the variant position of the probe reagents correspond to the variant position in the test molecules. In addition, an adjacent oligonucleotide, which can hybridize immediately 3' to either of the biotinylated oligonucleotides was synthesized. These reagents, in appropriate combinations, permit studying the effect of the ligase activity on any of the 16 possible base pairs, i.e. the four correct base pairs and the 12 mismatched nucleotide base pairs in a position immediately 5' to the junction between the two probe oligonucleotides. The assay was performed essentially as in example 1 except that the final concentration of NaCl and T4 DNA ligase in the assay was varied. As illustrated in FIG. 10A, this experiment demonstrates that it is possible to define a set of conditions under which any nucleotide mismatch can be discriminated from correct base pairing.

A similar experiment was conducted using the above except that oligonucleotide-172 was substituted with the pBR328:$\beta^A$=1.9 which contains the normal $\beta$-globin gene. The results of that experiment are shown in FIG. 10B.

EXAMPLE 6

This Example demonstrates that the assay of the present invention can be utilized when one of the probes (either the target or adjacent probe) is immobilized on a solid support prior to annealing and ligation.

Streptavidin agarose beads were added to wells of a microtiter plate as previously described in a volume of three ml of water. 140 fMols of B-131 (biotinylated) were added in 1 ul and allowed to react for approximately 10 minutes. Thereafter, linearized plasmid containing the $\beta^A$ globin gene (BR328:$\mu^A$1.9) or oligonucleotide-172 (with a sequence complementary to the contiguous probes 131 and 133) together with P-133 were added to the wells containing the agarose immobilized B-131 probe. As a control, the probe B-137 (FIG. 9) was also immobilized on streptavidin agarose. This probe is incapable of ligating with P-133 as there is a one nucleotide gap and terminal mismatch between the two probes when properly annealed to a test molecule containing the $\beta$-globin gene.

Figure 11:
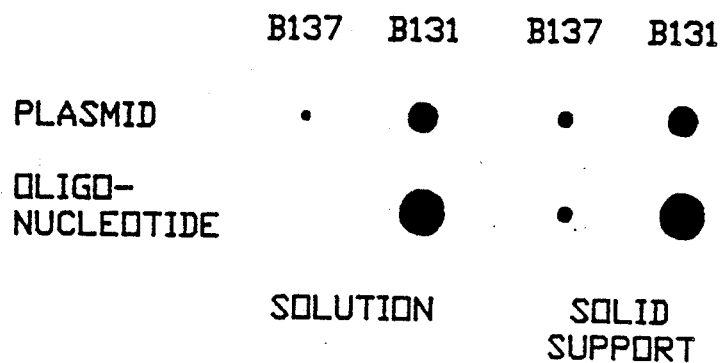
FIG. 11 illustrates the results obtained in Example 6.

The results of this experiment are shown in FIG. 11. As can be seen, a strong signal indicating ligation is observed when the B-131 probe is employed in conjunction with the normal $\beta$-globin DNA sequences together with P-133, whether the B-131 is immobilized prior to or after the annealing and ligation of the B-131 and P-133 probes. The minor signals shown for the B-137/P-133 probe set is attributed to nonspecific absorption of the labeled oligonucleotide. Thus, the assay of the present invention may be practiced in a heterogenous system.

EXAMPLE 7

In the previous Example, a target probe was immobilized on a solid support by way of an affinity linkage vis-a-vis the streptavidin-biotin interaction. This experiment describes the covalent immobilization of the target probe 131 to two different solid supports and the use of such immobilized probe in the assay of the present invention.

Oligonucleotide-131 was covalently attached to agarose beads by way of reaction between an active thiol group on the agarose beads with an active maleimidyl group on the oligonucleotide-131. The thiol containing agarose Bio Rad Affigel 401 was obtained from Bio Rad laboratories in Richmond, Calif.

Oligonucleotide-131 containing the active maleimidyl group was obtained by the aminothymidine residueusing the following procedure. Oligonucleotide-131 including a 5'terminal aminothymidine residue was synthesized as previously described and purified by reverse phase HPLC chromatography. This oligonucleotide was reacted with a fifty fold excess of succinimidyl-3-maleimidyl propionate (BMPS) (Molecular Probes, Junction City, Oreg.) in an aqueous solution containing 20% dimethylformamide and 100 mM sodium bicarbonate pH 9.0 for two hours at room temperature. The derivatized oligonucleotide-131 was purified by HPLC chromatography using the same conditions as set forth for the biotinylation of oligonucleotide-131.

The derivatized oligonucleotide-131 (10 nmoles) in 500 microliters of 1.0 M NaCl, 15 mM Tris, 1 mM EDTA, pH 8.0 was reacted with approximately 0.5 ml settled mmoles). After two hours at room temperature the supernatant was assayed by HPLC chromotography which indicated that virtually all of the derivatized oligonucleotide-131 was bound to the Affigel 401. To render them unreactive, residual sulfhydryl groups on the agarose were reacted with an equal volume of 10 mg iodoacetamide/ml in 1.0 M NaCl, 50 mM Tris, 1 mM and used to detect normal $\beta$-globin sequences as described in Example 6. The results of that experiment (not shown) were substantially the same as those obtained in Example 6.

Oligonucleotide-131 was also covalently linked to a second solid support. However, in this case an active sulfhydryl group oligonucleotide-131 was used to covalently link that oligonucleotide to a polymeric support having an active maleimidyl group. The polymeric support was Bio Rad Affi Prep 10 obtained from Bio Rad Laboratories, Richmond, Calif. This solid support was first derivatized by reacting with spermine for two hours at pH 7.5 to produce an amino derivative of the Affi Prep 10. This amino derivative was thereafter reacted with BMPS as previously described to produce an active maleimidyl polymeric support.

The thiol derivative of the oligonucleotide-131 was produced by the following procedures. Amino oligonucleotide-131 was reacted with an excess of succinimidyl-3-(pyridylodithio)propionate(SPDP) (Pierce Chemicals) to produce a disulfide derivative of oligonucleotide-131. This disulfide derivative was purified by reverse phase HPLC and lyophilized. The disulfide derivative was thereafter treated with 15 mM DTT and 0.2 M Tris, 1.0 M NaCl, 1mM EDTA, pH 8.5 at 37° C. for two hours. The resultant thiol oligonucleotide-131 was purified by HPLC as previously described.

Approximately 5 nmole of the thiol oligonucleotide-131 in HPLC buffer was added to an equal volume of 0.2 M Tris, 1.0 M NaCl, 1 mM EDTA, pH 8.5. Approximately 100 mg of the derivatized polymeric support was added and the reaction was allowed to proceed at room temperature for 5 approximately 4 hours. The supernatant was assayed by HPLC for the presence of residual sulfhydryl oligonucleotide-131 to ascertain the completion of the reaction. The residual reactive groups on the polymeric support were then neutralized by treatment with excess $\beta$-mercaptoethanol in the above pH 8.5 buffer for 2 hrs. at room temperature. The polymeric support containing oligonucleotide-131 covalently coupled to it was thereafter washed and used in the assay of $\beta^A$ globin DNA sequences as described in Example 6. The results of that experiment (not shown) were substantially similar to those obtained in Example 6.

Having described the preferred embodiments of the present invention, it will appear to those of ordinary skill in the art that various modifications may be made and that such modifications are intended to be within the scope of the present invention.

What is claimed is:

1. An assay for a biologically derived denatured DNA or RNA test substance, which has a known normal nucleotide sequence and a known possible mutation at at least one target nucleotide position in said sequence, which assay determines whether the test substance has said normal nucleotide sequence or said possible mutation, said assay comprising the steps of
   (a) annealing a target oligonucleotide probe of predetermined sequence to a first sequence of said test substance so that said target nucleotide position is aligned with a nucleotide in an end region of said target probe,
   (b) annealing an adjacent oligonucleotide probe of predetermined sequence to a second sequence of said test substance contiguous to said first sequence, so that the terminal nucleotide in said end region of said target probe and one end of said adjacent probe are directly adjacent to each other,
   (c) contacting said annealed target probe and adjacent probe with a linking agent under conditions such that the directly adjacent ends of said probes covalently bond to form a linked probe product unless there is nucleotide base pair mismatching between said target probe and said test substance at the target nucleotide position,
   (d) separating said test substance and linked probe product, if formed, and
   (e) detecting whether or not said linked probe product is formed as an indication of nucleotide base pair matching or mismatching at said target nucleotide position.

2. The assay of claim 1 in which said target probe or said adjacent probe is labeled and said detecting is performed by directly or indirectly detecting said label.

3. The assay of claim 2 in which said label is selected from the group consisting of a radioactive tag, an enzyme, a fluorescent tag, and a colorimetric tag.

4. The assay of claim 2 performed in a fluid medium in which only one of said target probe and said adjacent probe is labeled and the non-labeled one is immobilized, said method further comprising, prior to step (e), separating the immobilized linked probe product from the remainder of the fluid medium, and said detecting is performed by detecting the presence of said label contained by said immobilized linked probe product.

5. The assay of claim 4 wherein said target probe or said adjacent probe is immobilized by a covalent bond or by an affinity bond.

6. The assay of claim 2 wherein said test substance is immobilized.

7. The assay of claim 2 performed in a fluid medium in which only one of said target and said adjacent probes is labeled and in which both of said probes are in solution during steps (a), (b), and (c), said method further comprising immobilizing the non-labeled probe before step (e), and said detecting is performed by detecting the presence of said label on said immobilized linked probe product.

8. The assay of claim 1 together with the steps of (f) annealing a second adjacent oligonucleotide probe of predetermined sequence to a third sequence of said test substance contiguous with the end of said target or said adjacent probe opposite its facing end, and
(g) contacting said second adjacent probe with a linking agent to link it with said contiguous target or said adjacent probe.

9. The assay of claim 1 in which said linking agent is a ligase, and said linking occurs by ligation.

10. The assay of claim 2 together with the step of (f) placing the reaction mixture of step (d) in a migration medium in which said target and said adjacent probes individually migrate at substantially different rates than said linked probe product, and in which said detecting occurs by detecting the position of labeled probe in said migration medium as a function of time.

11. The assay of claim 1 further comprising the step of:
(f) annealing to a second test substance a second oligonucleotide probe with substantially the same sequence as said target probe except that it contains a different nucleotide in at least one of said end nucleotide positions, said target and said second probes being labeled with different labels, wherein said detection step distinguishes between said labels.

12. The assay of claim 1 in which the normal nucleotide is present at said target nucleotide position.

13. The assay of claim 1 in which a mutant nucleotide is present at said target nucleotide position.

14. The assay of claim 1 in which said test substance is formed of DNA.

15. The assay of claim 1 in which said test substance is formed of RNA.

16. The assay of claim 1 wherein said end region of said target probe consists of the end nucleotide of said target probe and the three nucleotides adjacent to it.

17. The assay of claim 1 wherein said end region of said target probe consists of the end nucleotide of said target probe and the nucleotide adjacent to it.

18. The assay of claim 1 wherein said test substance comprises DNA sequences derived from genomic DNA.

19. The assay of claim 18 wherein said DNA sequences include sequences encoding all or part of normal β-globin or sickle β-globin gene.

20. A kit for assaying a biologically derived denatured DNA or RNA test substance which has a known normal nucleotide sequence and a known possible mutation at at least one target nucleotide position in said sequence, said kit being useful for determining whether the test substance has said known normal nucleotide sequence or said possible mutation, said kit comprising
(a) a first oligonucleotide probe capable of serving as a target probe of predetermined nucleotide sequence capable of annealing to a first sequence of said test substance, said target probe having at least one nucleotide position in an end region of said target probe which is complementary to the normal nucleotide or said possible mutation at said target nucleotide position, and
(b) a second oligonucleotide probe capable of serving as an adjacent probe of predetermined sequence capable of annealing to a second sequence of said test substance contiguous to said first sequence such that the terminal nucleotide in said end region of said target probe and one end of said adjacent probe are directly adjacent to each other, said target or adjacent probes being labeled.

21. The kit of claim 20 further comprising
(c) a linking agent for covalently bonding said target and adjacent probes.

22. The kit of claim 20 in which said label is selected from the group consisting of a radioactive tag, an enzyme, a fluorescent tag and, a colorimetric tag.

23. The kit of claim 20 in which only one of said target and adjacent probes is labeled and the non-labeled one is immobilized.

24. The kit of claim 20 in which the labeled oligonucleotide is soluble.

25. The kit of claim 20 in which only one of the target and adjacent probes is labeled, both said target and adjacent probes are soluble, and the non-labeled one is bound to a first binding moiety capable of binding with a second binding moiety complementary to said first binding moiety.

26. The kit of claim 21 further comprising an immobilized second binding moiety complementary with said first binding moiety.

27. The kit of claim 20 further comprising means for detecting the label.

28. The kit of claim 20 further comprising an electrophoretic medium.

* * * * *